(12) United States Patent
Tanaka et al.

(10) Patent No.: US 8,647,668 B2
(45) Date of Patent: *Feb. 11, 2014

(54) TABLET QUICKLY DISINTEGRATING IN ORAL CAVITY

(75) Inventors: Nobukazu Tanaka, Toyama (JP); Yoshiro Nagai, Toyama (JP); Hiroshi Kawaguchi, Toyama (JP); Tadashi Fukami, Toyama (JP); Terumasa Hosokawa, Toyama (JP)

(73) Assignee: Fuji Chemical Industry Co., Ltd., Nakaniikawa-gun (JP)

( * ) Notice: Subject to any disclaimer, the term of this patent is extended or adjusted under 35 U.S.C. 154(b) by 1017 days.

This patent is subject to a terminal disclaimer.

(21) Appl. No.: 10/576,257

(22) PCT Filed: Oct. 14, 2004

(86) PCT No.: PCT/JP2004/015151
§ 371 (c)(1),
(2), (4) Date: Apr. 27, 2007

(87) PCT Pub. No.: WO2005/037254
PCT Pub. Date: Apr. 28, 2005

(65) Prior Publication Data
US 2007/0275058 A1     Nov. 29, 2007

(30) Foreign Application Priority Data

Oct. 15, 2003   (JP) .................. 2003-355076
Aug. 16, 2004   (JP) .................. 2004-236594

(51) Int. Cl.
*A61K 9/20*    (2006.01)

(52) U.S. Cl.
USPC ........................................ 424/465

(58) Field of Classification Search
USPC ........................................ 424/465
See application file for complete search history.

(56) References Cited

U.S. PATENT DOCUMENTS 5,466,464 A * 11/1995 Masaki et al. ............. 424/434
2005/0106240 A1   5/2005 Tanaka et al.

FOREIGN PATENT DOCUMENTS

| JP | 5-271054 | 10/1993 |
|---|---|---|
| JP | 5-310558 | 11/1993 |
| JP | 10-120554 | 5/1998 |
| JP | 2000-86537 | 3/2000 |
| JP | 2001-253818 | 9/2001 |
| JP | 2002-128661 | 5/2002 |
| JP | 2002-154988 | 5/2002 |
| JP | 2003-176242 | 6/2003 |
| WO | 95/20380 | 8/1995 |
| WO | 00/78292 | 12/2000 |
| WO | 01/89485 | 11/2001 |
| WO | 02/30400 | 4/2002 |
| WO | 02/69934 | 9/2002 |
| WO | 02/92057 | 11/2002 |
| WO | 03/009831 | 2/2003 |
| WO | 03/074085 | 9/2003 |

OTHER PUBLICATIONS

Ishikawa, Preparation of Rapidly Disintegrating Tablet Using New Types of Microcrystalline Cellulose (PH-M Series) and Low Substituted-Hydroxypropylcellulose or Spherical Sugar Granules by Direct Compression Method, Chem. Pharm. Bull., vol. 49, No. 2, pp. 134-139, 2001.*
Database WPI Section Ch, Week 200260, Derwent Publications Ltd., London, GB; AN 2002-560764, XP002415206 & JP 2002 128661 A (Chugai Pharm), May 9, 2002.
U.S. Appl. No. 12/908,225, filed Oct. 20, 2010, Tanaka, et al.
Japanese Office Action dated Nov. 9, 2010 as received in the corresponding Japanese Patent Application No. 2005-514774.

* cited by examiner

*Primary Examiner* — Frederick Krass
*Assistant Examiner* — Adam C Milligan
(74) *Attorney, Agent, or Firm* — Oblon, Spivak, McClelland, Maier & Neustadt, L.L.P.

(57) ABSTRACT

The present invention provides rapid disintegrating tablets in oral cavity having a shortened disintegration time in oral cavity as well as a sufficient hardness compared to rapid disintegrating tablets of the prior art. The above objective is solved by a composition in which the inorganic excipient and the disintegrating agent are dispersed in the complex particles consisting of mannitol and other saccharide(s) in a specific ratio, and rapid disintegrating tablets in oral cavity obtained by direct compression of the composition.

18 Claims, No Drawings

TABLET QUICKLY DISINTEGRATING IN ORAL CAVITY

TECHNICAL ART

The present invention relates to a composition for a rapid disintegrating tablet in oral cavity and also to a rapid disintegrating tablet in oral cavity prepared by direct tabletting of the composition.

BACKGROUND ART

With regard to solid preparations for oral administration, rapid disintegrating tablets in oral cavity which are rapidly disintegrated or dissolved when placed in oral cavity have been known.

As such rapid disintegrating tablets in oral cavity, there have been known, e.g., those containing an excipient and erythritol (Japanese Unexamined Patent Publication No. 2003-176242), those prepared by spray-drying a suspension containing an aqueous medium, calcium hydrogen phosphate and saccharides (WO 99/55373), those prepared by spray-drying a suspension containing an inorganic excipient and saccharides (Japanese Unexamined Patent Publication No. 2000-86537), those prepared by spray-drying a dispersion containing an inorganic antacid, a sugar alcohol and a disintegrating agent in an aqueous medium (Japanese Unexamined Patent Publication No. Hei 10(1998)-120554).

Besides the above, there have been disclosed a method for the production of oral dissolving tablets wherein saccharides such as xylitol, a pharmacologically active ingredient and water are mixed and made into tablets (Japanese Unexamined Patent Publication No. Hei 5(1993)-271054), an orally dissolving compression-molded product comprising granulates prepared by a fluidized-bed granulation of saccharides having a low molding property together with saccharides having a high molding property as binders (WO 95/20380), a rapid disintegrating solid preparation containing an active ingredient, a saccharide having an average particle diameter of 5 μm to 90 μm, a saccharide having an average particle diameter of 90 μm to 500 μm, a disintegrating agent and cellulose (WO 00/78292), a rapid disintegrating solid preparation prepared by spray-drying one sugar alcohol and a disintegrating agent, followed by dry tabletting (WO 02/69934), etc.

DISCLOSURE OF THE INVENTION

An object of the present invention is to provide a composition suitable for preparing rapid disintegrating tablets in oral cavity where, as compared with the rapid disintegrating tablets in oral cavity in the prior art as above, oral disintegration time is greatly shortened and a sufficient hardness is available in spite of the use of a direct compression by a common tabletting machine, and also to provide rapid disintegrating tablets in oral cavity using the above composition.

The present inventors have noted as a result of investigations in compositions for rapid disintegrating tablets in oral cavity: in order to immediately disintegrate the obtained tablet in saliva or small amount of water in oral cavity, it is necessary to prepare tablets in which binding force among particles is weak and void fraction is large and it is necessary to have properties which are contrary to those for preparing tablets having hardness which is no problem in practical use. Moreover, they have found that there are room for improvement, i.e. that although the conventional noncrystalline solid of saccharides which are formed by spray-drying greatly contribute in improving the molding property, they have negative effect for disintegration and dissolution in the oral cavity causing a delay in disintegration, and cause tabletting troubles (such as sticking) in molding the tablets, that lowering of fluidity of the composition depending on type and quantity of the saccharide occurs as well as lowering of recovery rate of the composition itself occurs.

In order to achieve the above-mentioned object, the present inventors have conducted intensive studies and found that complex particles containing mannitol and other saccharide(s) in an optimum compounding ratio and being prepared by dissolving partly or all amount of mannitol together with all amount of other saccharide(s) have an improved compression molding property and an improved dissolving rate. They have also found that, when fine disintegrating agent and inorganic excipient are homogeneously dispersed in the complex particles of the saccharides, it is now possible to give a composition having both improved compression molding property and rapid disintegration of the resulting tablets in the mouth. As a result, the present invention has been achieved.

It has been also found that, with regard to a composition containing mannitol and other saccharide(s) in a specific compounding rate, an endothermic peak of saccharides (mannitol and other saccharide(s)) which is measured by a differential scanning calorimeter (hereinafter, abbreviated as DSC) shifts to a low-temperature side as compared with an endothermic peak of mannitol only. Similar shifts to low-temperature side were also found in several kinds of saccharides and there were some saccharides such as erythritol which shows depression of 50° C. or more when the compounding ratio was changed. As a result of investigations, it has been found that, when shift of endothermic peak to the low-temperature side of saccharide in a composition comprising mannitol and other saccharide(s) is 0.5 to 10° C. in a specific compounding ratio of the saccharides, molding force and disintegrating force which are the properties being contrary to each other show the maximum effects.

A composition for rapid disintegrating tablets in oral cavity according to the present invention comprises components (a) to (c) in such a manner that (a) saccharides consisting of a combination of mannitol and other saccharide(s) are 40 to 90 parts by weight;

(b) an inorganic excipient is 1 to 30 part(s) by weight; and (c) a disintegrating agent is 5 to 40 parts by weight provided that total amount of components (a), (b) and (c) is 100 parts by weight.

The above-mentioned composition is characterized in that it achieves the maximum effect as a composition for rapid disintegrating tablets in oral cavity when (1) mannitol and other saccharide(s) in a specific ratio form complex particles or, preferably, form a solid dispersion, (2) fine disintegrating agent and inorganic excipient are homogeneously dispersed, (3) the composition is prepared by a spray-drying method in which the condition thereof is such that all components are homogeneously dispersed, and (4) endothermic peak of the saccharides measured by a differential scanning calorimeter (DSC) shifts to a low-temperature side to an extent of 0.5 to 10° C.

The rapid disintegrating tablets in oral cavity according to the present invention obtained from the above composition comprises 0.01 to 100 parts by weight of a pharmacologically active ingredient and 0.01 to 1000 parts by weight of a component which does not deteriorate a disintegrating property based on 100 parts by weight of the above-mentioned composition.

The term "rapid disintegrating tablet in oral cavity" used herein means a tablet which is able to be disintegrated in the oral cavity rapidly, for example, within 40 seconds, preferably within 30 seconds, more preferably within 20 seconds. The oral disintegration time used herein is the time which is measured by the measuring method mentioned in the Examples shown below.

BEST MODE FOR CARRYING OUT THE INVENTION

It is preferred that, in the composition of the present invention, an inorganic excipient and a disintegrating agent are homogeneously dispersed in complex particles comprising mannitol and other saccharide(s). The complex particles comprising mannitol and other saccharide(s) include those which form a solid dispersion of mannitol with other saccharide(s). The complex particles are in such a state that, in a crystalline or noncrystalline structure of mannitol, other saccharide(s) having nearly the same molecular size and shape as mannitol molecule is/are mixed as an assembly with molecule or several molecule(s) and, since they have poor regularity than pure substance, phenomena such as melting point depression and changes in solubility in water are resulted.

In the above-mentioned composition, shift of the endothermic peak of the saccharides to low-temperature side as measured by a DSC is 0.1 to 20° C., preferably 0.5 to 10° C. and a composition showing such a shift has excellent molding property and excellent disintegration of the resulting tablets. In the composition of the present invention, its shift of endothermic peak of the saccharides to the low-temperature side is about 0.5° C. when mannitol and sorbitol are contained in a ratio of mannitol:sorbitol is 97:3 (by weight) while it is about 10° C. when they are contained in a ratio of mannitol:sorbitol is 82:18 (by weight).

A phenomenon of shift of endothermic peak to low-temperature side as compared with that of sole mannitol as a result of formation of a solid dispersion of mannitol with other saccharide(s) in the composition of the present invention is believed to be a molar depression of freezing point. That is supported by the fact that, when other saccharide(s) are added in the same weight, a substance having small molecular weight shows bigger shift to the low-temperature side than a substance having big molecular weight.

In general, melting point is greatly affected by the degree of easiness of arrangement of molecules. In addition, in the formation of crystals, regularity of the constituting molecules is required and, in forming the crystals, it is necessary that the constituting molecules are uniform whereby, principally, crystals are able to be formed from the molecules of the same species. However, even in the case of different species, it is possible to form crystals where plural molecular species are mixed provided that their sizes and shapes are nearly the same and such crystals are known as a solid dispersion. In the solid dispersion as such, regularity is poor as compared with pure substance and, therefore, phenomena such as depressing of melting point occur as compared with the pure substance.

The fact that endothermic peak of the saccharide in the composition shifts to the low-temperature side shows that mannitol is in a distorted state while it still maintains its crystalline structure to some extent and that crystalline state of mannitol is in a state of somewhat high energy. By making into such a high-energy state, a change is resulted in properties of mannitol, i.e. "low molding property and low solubility", and properties of the saccharide, i.e. molding property and solubility (dissolving rate), are able to be improved.

Since fine disintegrating agent and inorganic excipient are homogeneously dispersed in the composition of the present invention, the tablets prepared from the composition has the optimum structure for introducing little water existing in oral cavity into the tablet as much as possible and much quicker. In the tablets obtained from the composition, water-introducing pores of the specific inorganic excipient and fine cavities of the tablets obtained from the composition which are formed by spray-drying introduce a small amount of water into the tablets and such water effectively act on the disintegrating agent dispersed in the tablet. Thus, rapid disintegrating effect in oral cavity is obtained.

In the composition of the present invention, inorganic excipient and disintegrating agent are not coagulated each other but are dispersed in the above-mentioned complex particles. Such a dispersed state is able to be observed under a scanning microscope.

With regard to the saccharide [component (a)] comprised in the composition of the present invention, a mixture of mannitol and other saccharide(s) is used. These saccharides are used in an amount of 40 to 90 parts by weight, preferably 50 to 80 parts by weight, more preferably 65 to 80 parts by weight based on 100 parts by weight of the total amount of the composition.

Ratio by weight of mannitol to other saccharide(s) as the saccharides is preferably such that mannitol:other saccharide(s)=(98 to 67):(2 to 33), more preferably mannitol:other saccharide(s)=(97 to 75):(3 to 25), still more preferably mannitol:other saccharide(s)=(96 to 81):(4 to 19).

Mannitol is usually used for obtaining powdery compositions having low hygroscopicity and high fluidity, however, its molding property is poor and its solubility is low as well and, therefore, when it is used in a composition for rapidly disintegrating tablets, a balance between the oral disintegration time and the hardness of the resulting tablets has not been sufficient. However, the present inventors have found that, when mannitol is used in a specific ratio with other saccharide(s), greatly decreased oral disintegration time and a good hardness are obtained.

With regard to other saccharide(s) in the present invention, any substance may be used so far as that, when it is made into complex particles together with mannitol, shift of the endothermic peak of the saccharides to the low-temperature side is able to be confirmed and that molding property and solubility of the resulting composition are able to be improved. Examples thereof are sorbitol, maltitol, lactitol, erythritol, xylitol, lactose, sucrose, glucose, fructose, maltose, trehalose, paratinit and paratinose. Preferred are sorbitol, maltitol, erythritol, lactose, sucrose, glucose, fructose, maltose and trehalose. All of the saccharides exemplified here are able to result in the melting point depression of mannitol when used together with mannitol.

The use of mannitol having an average particle diameter of 0.1 to 500 μm, preferably 0.1 to 100 μm and, more preferably, 0.5 to 30 μm is preferred because the rough feeling in oral cavity can be prevented. However, since other saccharide(s) is always dissolved during the manufacture of the composition, one having any average particle diameter may be used.

The inorganic excipient [component (b)] comprised in the composition of the present invention is 1 to 30 part(s) by weight, preferably 2 to 15 parts by weight, more preferably 3 to 10 parts by weight based on 100 parts by weight of the total amount of the composition.

The specific inorganic excipient according to the present invention has an average pore diameter of 100 nm or less and is preferred to be a pharmaceutically acceptable inorganic compound containing any of aluminum, magnesium and calcium. Such inorganic excipient is preferably, for example, magnesium aluminometasilicate, magnesium aluminosilicate, calcium hydrogen phosphate, calcium phosphate, precipitated calcium carbonate, dry aluminum oxide gel, hydrotalcite, magnesium silicate, synthetic aluminum silicate, calcium silicate and talc; any of them may be used solely or a mixture of two or more thereof may be used.

It is more preferred to use one or more selected from magnesium aluminometasilicate, calcium hydrogen phosphate, calcium carbonate, synthetic hydrotalcite, calcium silicate and talc.

It is preferred that the above-mentioned inorganic excipient has an average particle diameter of preferably 60 μm or less, more preferably 20 μm or less due to a homogeneous dispersing property in the composition of the present invention and also to prevention of the rough feeling in the mouth. It is possible to use a product which is subjected to pulverization by a common method for achieving the desired average particle diameter.

In the composition of the present invention, the disintegrating agent [component (c)] comprised in the composition of the present invention is 5 to 40 parts by weight, preferably 10 to 35 parts by weight, more preferably 17 to 34 parts by weight based on 100 parts by weight of the total amount of the composition.

The disintegrating agent is preferred to be selected from crospovidone, croscarmellose sodium, carboxystarch sodium, low-substituted hydroxypropyl cellulose and crystalline cellulose and, although any of them may be used solely, it is preferred to use a mixture of two or more thereof. It is especially preferred to use crospovidone and crystalline cellulose. Average particle diameter of the disintegrating agent is preferably 60 μm or less, more preferably 20 μm or less, due to homogeneous dispersing property in the composition and also to prevention of the rough feeling in oral cavity.

When crospovidone and crystalline cellulose are used as the disintegrating agent, crospovidone is contained, based on 100 parts by weight of the total amount of the composition, preferably 5 to 15 parts by weight, more preferably 5 to 13 parts by weight while crystalline cellulose is contained, based on the total weight of the composition, preferably 8 to 22 parts by weight, more preferably, 12 to 21 parts by weight.

Besides the saccharide, the inorganic excipient and the disintegrating agent, the composition of the present invention may comprise a pharmacologically active ingredient and/or a component which does not deteriorate the disintegrating property.

The pharmacologically active ingredient can be compounded in an amount of 0.01 to 100 part(s) by weight, preferably 0.01 to 67 part(s) by weight or, more preferably, 0.01 to 60 part(s) by weight based on 100 parts by weight of the total amount of the saccharide, the disintegrating agent and the inorganic excipient.

The composition of the present invention is able to be produced by compounding the pharmacologically active ingredient with the saccharide, the inorganic excipient and the disintegrating agent.

The component which does not deteriorate the disintegrating property can be compounded in an amount of 0.01 to 1,000 part(s) by weight or, preferably, in 0.1 to 500 part(s) by weight to 100 parts by weight of the total amount of the saccharide, the disintegrating agent and the inorganic excipient. The composition of the present invention can be produced by compounding the component which does not deteriorate the disintegrating property with the saccharide, the inorganic excipient and the disintegrating agent.

The composition of the present invention can be manufactured by a production method by which the desired physical property of the composition of the present invention is able to be achieved and commonly used methods such as a spray-drying method, a fluidized bed granulation and drying method, a stirring granulation method and a wet-type method (e.g., a wet-type extrusion granulation method) may be employed. A spray-drying method is preferred in view of the fact that the production method is simple and that desired physical property is apt to be achieved.

The composition of the present invention can be produced by spray-drying an aqueous solution or an aqueous dispersion containing the components (a) to (c) according to a common method. More specifically, it can be produced in such a manner that mannitol and other saccharide(s) are dissolved or dispersed in advance in an aqueous medium, the disintegrating agent and the inorganic excipient are homogeneously dispersed therein and the resulting dispersion is spray-dried. The expression reading "mannitol and other saccharide(s) are dissolved or dispersed in advance in an aqueous medium" means the following. Thus, it is sufficient that at least a part of mannitol and at least a part of other saccharide(s) are dissolved in the aqueous medium and that remaining parts of mannitol and other saccharide(s) may either be dissolved or dispersed. For the purpose that mannitol and other saccharide(s) form a solid dispersion, it is preferred that a part of mannitol and all of other saccharide(s) are dissolved therein.

With regard to the above-mentioned aqueous medium, any medium may be used so far as it does not affect on the physical property of the composition and which is pharmaceutically acceptable, examples thereof being water, ethanol and methanol.

There is no particular limitation for the condition of spray-drying. However, with regard to a spray-dryer, it is preferred to use a spray-dryer of a disk type or a nozzle type. With regard to the temperature for spray-drying, it is preferred that the inlet temperature is about 120 to 210° C. and the outlet temperature is about 80 to 130° C. With regard to the solid concentration of the aqueous dispersion upon spray-drying, it may be within a range by which the spray-drying is feasible and it is usually 10 to 50% by weight and, preferably 25 to 45% by weight.

Average particle diameter of the composition of the present invention obtained by spray-drying as mentioned above can be appropriately adjusted depending upon concentration of the aqueous solution or aqueous dispersion, spray-drying method, drying condition, etc. and, when it is 1 to 500 μm, preferably 5 to 300 μm, more preferably 10 to 200 μm, a rough feeling in oral cavity can be prevented whereby that is preferred. A specific volume of the composition is preferably about 1.5 to 2.5 g/ml, and a repose angle is preferably about 30 to 42°.

The rapid disintegrating tablets in oral cavity according to the present invention comprises 0.01 to 100 part(s) by weight, preferably 0.01 to 67 part(s) by weight or, more preferably, 0.1 to 60 part(s) by weight of the pharmacologically active ingredient based on 100 parts by weight of the composition obtained as above.

With regard to the pharmacologically active ingredient to be used in the present invention, one which is coated by a known method may be used when it has bitter taste. It may also be subjected for controlled release by a known method for effecting release thereof in digestive tracts.

Any form including solid, crystalline, oil, solution and the like, of the pharmacologically active ingredient may be used in the present invention. The use thereof is not particularly limited and one or more ingredient(s) selected from the followings is/are used; for example, central nerve system acting drugs such as agent for peripheral nerve, antipyretic/analgesic/anti-inflammatory agent, hypnotic/analgesic agent, agent for psychological nerve, psychotropic agent, antianxiety agent, antidepressant, hypnotic/analgesic agent, antiepileptic agent, sympathomimetic agent and antispasmodic; drugs for peripheral nerve such as skeletal muscle relaxant and autonomic agent; drugs for circulatory organs such as bronchodilator, cardiotonic, agent for arrhythmia, diuretic, respiratory stimulant and vasodilator; drugs for respiratory organs such as bronchodilator and antitussive; pharmaceuticals for digestive tracts such as digestive, antiflatuent, antiulcer agent and antacid; metabolic drugs such as brain metabolic stimulant, hormone preparation, anti-histaminic agent and vitamin preparation; antiulcer agent; antibiotic; chemotherapeutic; extract of traditional oriental medicines; nutritional and tonic medicine; medicine for allergy; and microbes.

As the pharmacologically active ingredient, active ingredients of cold medicine and active ingredient for rhinitis may also be mentioned. Examples of the active ingredient of cold medicine are antipyretic/analgesic/anti-inflammatory agent, bronchodilator, antihistaminic agent, antitussive agent, expectorant, antitussive/expectorant, vitamin preparation and extract of traditional Chinese medicines. Examples of the active ingredient for rhinitis are sympathetic stimulant, parasympatholytic agent, anti-allergic agent and anti-inflammatory agent. Examples of the antipyretic/analgesic/anti-inflammatory agent are aniline derivatives such as acetaminophen, phenacetin and lefetamine hydrochloride; salicylic acid derivatives such as ethenzamide, sasapyrine, methyl salicylate, phenyl salicylate, sodium salicylate, choline salicylate, aspirin and aluminum aspirin; pyrazolone derivatives such as isopropylantipyrine, sulpyrine, phenylbutazone, ketophenylbutazone, antipyrine and aminopyridine; propionic acid derivatives such as ibuprofen, ketoprofen, oxaprozin, naproxen, calcium fenoprofen and tiaprofenic acid; phenylacetic acid derivatives such as fenbufen, diclofenac sodium and amfenac sodium; indoleacetic acid derivatives such as indomethacin, indomethacin farnesil, proglumetacin maleate and tolmetin sodium; anthranylacetic acid derivatives such as mefenamic acid, fluphenamic acid and tolfenamic acid; oxicam derivatives such as piroxicam, ampiroxicam and tenoxicam; benzidamine hydrochloride; epirizole (mepirizole); tinoridine hydrochloride; tiaramide hydrochloride; anti-inflammatory enzyme preparation; Serapeptidase (trade name); and lysozyme chloride. These antipyretic/analgesic/anti-inflammatory agents may be used solely or two or more thereof may be used jointly.

Examples of the bronchodilator are ephedrine hydrochloride, dl-methylephedrine hydrochloride, dl-methylephedrine hydrochloride saccharinate, isoprenaline hydrochloride, isoproterenol sulfate, methoxyphenamine hydrochloride, orciprenaline sulfate, chlorprenaline hydrochloride, trimetoquinol hydrochloride, salbutamol sulfate, terbutaline sulfate, hexoprenaline sulfate, formoterol fumarate, fenoterol hydrobromide, procaterol hydrochloride, pruterol hydrochloride, clenbuterol hydrochloride, mabuterol hydrochloride, xanthine derivatives such as aminophylline, theophylline, diprophylline and proxyphylline and anticholinergic agent such as flutropium bromide and oxitropium bromide. Examples of the antihistaminic agent are antihistaminic agent of an ethanolamine type such as diphenhydramine, antihistaminic agent of a propylamine type such as dl-chlorpheniramine maleate and d-chlorpheniramine maleate, antihistaminic agent of a phenothiazine type such as alimemazine tartrate, isothipendyl hydrochloride, promethazine hydrochloride and mequitazine, diphenylpyraline, carbinoxamine maleate, clemastine fumarate, iproheptine hydrochloride, homochlorcyclizine hydrochloride, cyproheptadine hydrochloride, dimethindene maleate and triprolidine hydrochloride.

Examples of the antitussive agent are codeines such as codeine phosphate and dihydrocodeine phosphate, dextromethorphan hydrobromide, cloperastine, noscapine dimemorfan, oxeladin, pentoxiverin citrate, eprazinone hydrochloride, clobutinol hydrochloride, isoaminile citrate, fominoben hydrochloride, clofedanol hydrochloride, benproperine phosphate, hydrocotarnine and dibunate sodium.

Examples of the expectorant are potassium guiacolsulfonate, cysteine derivatives such as carbocysteine, L-ethylcysteine hydrochloride, L-methylcysteine hydrochloride and acetylcysteine, bromhexine and ambroxol hydrochloride. Examples of the antitussive/expectorant are guaifenesin, tipepidine, oxymethebanol, alloclamide hydrochloride, carbetapentane phenate, trimethoquinol hydrochloride and methoxyphenamine hydrochloride. Incidentally, the pharmacologically active ingredients which are exemplified hereinabove as antitussive, expectorant and antitussive/expectorant sometimes exhibit antitussive action and/or expectorant action in a complexed manner.

Examples of the psychotropic agent are chlorpromazine and reserpine. Examples of the anti-anxiety agent are alprazolam, chlordiazepoxide and diazepam. Examples of the antidepressant are maprotiline hydrochloride, imipramine, amphetamine and metafetan. Examples of the hypnotic/sedative agent are estazolam, nitrazepam, diazepam, perlapin and Phenobarbital sodium. Examples of the antispasmodic agent are scopolamine hydrobromide, papaverine hydrochloride and diphenhydramine hydrochloride. Examples of agent acting on central nerve are citicoline, etc. Examples of the antiepileptic agent are phenytoin and carbamazepine. Examples of the sympathomimetic agent are isoproterenol hydrochloride, etc.

The gastrointestinal drug includes, for example, digestant such as diastase, saccharated pepsin, scopolia extract, cellulose AP3, lipase AP and cinnamon bark oil and antiflatuent such as berberine chloride, Lactobacillus and Bifidobacterium. Examples of the antacid are magnesium carbonate, sodium hydrogen carbonate, magnesium aluminometasilicate, magnesium aluminosilicate, synthetic hydrotalcite, precipitated calcium carbonate and magnesium oxide. Examples of the antiulcer agent are famotidine, lansoprazole, omeprazole, rabeprazole, cimetidine and ranitidine hydrochloride.

Examples of medicine for allergy are amlexanox and seratrodast. Examples of the antitussive/expectorant are chloperastine hydrochloride, dextromethorphan hydrobromide, theophyline, potassium guaiacolsulfonate, guaifenesin and codeine phosphate. Examples of the antiemetic drug are difenidol hydrochloride and metoclopramide. Examples of the respiratory stimulant are levallorphan tartrate, etc. Examples of dental/oral drug are oxytetracycline, triamcinorone acetonide, chlorhexidine hydrochloride and lidocaine. Examples of antihistamic agent are diphenhydramine hydrochloride, promethazine, isothipendyl hydrochloride and dl-chlorpheniramine maleate.

Examples of the cardiotonic agent are caffeine and digoxin. Examples of the anti-arrhythmic agent are procainamide hydrochloride, propranolol hydrochloride and pindolol. Examples of the diuretic agent are isosorbide, furosemide and hydrochlorothiazide. Examples of the hypotensive agent are delapril hydrochloride, captopril, hydralazine hydrochloride, labetalol hydrochloride, manidipine hydrochloride, candesartan cilexetil, methyldopa and perindopril erbumine. Examples of angiotonic are phenylephrine hydrochloride, etc. Examples of coronary vasodilator are carbocromen hydrochloride, molsidomine and verapamil hydrochloride. Examples of the peripheral blood vessel dilator are cinnarizine, etc. Examples of the agent for hyperlipemia are cerivastatin sodium, simvastain, pravastatin sodium and atorvastatin calcium hydrate.

Examples of the antibiotic are cephem antibiotic such as cephalexin, cefaclor, amoxicillin, pivmecillinam hydrochloride, cefotiam hexetil hydrochloride, cefadroxil, cefixime, cefditoren pivoxil, cefteram pivoxil and cefpodoxime proxetil; synthetic antibacterial agent such as ampicillin, ciclacillin, nalidixic acid and enoxacin; monobactam antibiotics such as carumonam sodium; penem antibiotics; and carbapenem antibiotics.

Examples of the antidiabetic agent are tolbutamide, voglibose, pioglitazone hydrochloride, glibenclamide and troglitazone.

Examples of the antispasmodic agent are meclizine hydrochloride and dimenhydrinate.

Examples of the anti-rheumatic agent are methotrexate and bucillamine.

Examples of the hormone preparation are liothyronine sodium, dexamethasone sodium phosphate, prednisolone, oxendolone and leuprorelin acetate.

Examples of the alkaloidal narcotic are opium, morphine hydrochloride, thoron, oxycodone hydrochloride, opium alkaloid hydrochloride and cocaine hydrochloride.

Examples of the sulfa drug are sulfisomidine and sulfamethizole.

Examples of the drug for treatment of gout are allopurinol and cholchicine.

Examples of the anticoagulant are dicumarol, etc.

Examples of the agent for malignant tumor are 5-fluorouracil, uracil, mitomycin, manidipine hydrochloride, voglibose, candesartan cilexetil and pioglitazone hydrochloride.

Examples of vitamin are carotenoid such as astaxanthin, vitamin A, β-carotene, lutein and zeaxanthin; vitamin B1 or derivative thereof or salt thereof such as fursultiamine, fursultiamine hydrochloride, prosultiamine, octotiamine, thiamine disulfide, bisbentiamine, bisbutyltiamine, bisibutiamine, benfotiamine and cetotiamine hydrochloride; vitamin B2 or derivative thereof or salt thereof such as riboflavin, riboflavin sodium phosphate, flavin adenine dinucleotide sodium and riboflavin butyrate; vitamin C derivative such as ascorbic acid, ascorbic acid glucoside, L-ascorbyl palmitate and L-ascorbic acid phosphate; vitamin E such as tocopherol, tocopherol acetate, tocopherol succinate, tocopherol nicotinate and tocotrienol; etc.

Depending upon the type of the pharmacologically active ingredient used, there is a possibility that the range of amount of the component in the composition of the present invention capable of providing a rapid disintegrating property in the mouth varies and such variation is also within a scope of the present invention.

Rapid disintegrating tablets in oral cavity of the present invention can comprise, besides the pharmacologically active ingredient, 0.01 to 2000 parts by weight, preferably 0.01 to 1000 parts by weight of a component which does not deteriorate a disintegrating property based on 100 parts by weight of the composition obtained as above.

The component which does not deteriorate the disintegrating property and which can be added to the composition of the present invention and/or to the rapid disintegrating tablets in oral cavity of the present invention may be the one which is pharmaceutically acceptable and includes excipient (such as erythritol, sorbitol, lactose and the like saccharides, carboxymethylcellulose calcium, hydrogenated oil and talc), surfactant (such as polyoxyethylene hydrogenated castor oil, polyoxyethylene polyoxypropylene glycol, sorbitan fatty acid ester, polysorvate, fatty acid glycerol ester and sodium lauryl sulfate), binder (such as hydroxypropyl cellulose, alginic acid, gelatin, partial pregelatinized starch, povidone, gum acacia, pullulan and dextrin), lubricant (stearic acid, magnesium stearate, calcium stearate, sucrose fatty acid ester, polyethylene glycol and stearyl fumarate sodium), acidifier (such as citric acid, tartaric acid, malic acid and ascorbic acid), foaming agent (such as sodium hydrogen carbonate and sodium carbonate), sweetener (such as saccharine sodium, dipotassium glycyrrhizin, aspartame, stevia and thaumatin), flavor (such as lemon oil, orange oil and menthol), coloring agent (such as food dye Red No. 2, food dye Blue No. 2, food dye Yellow No. 5, lake dye for food and iron sesquioxide), stabilizer (such as sodium edetate, tocopherol and cyclodextrin), corrigent and flavoring agent. These components may be added to such an extent that they do not deteriorate the rapid disintegrating property of the tablets of the present invention.

The rapid disintegrating tablets in oral cavity of the present invention can be produced by compression molding a mixture obtained by mixing the pharmacologically active ingredient and the component which does not deteriorate the disintegrating property to the above composition. The compression molding is preferably carried out by a direct tabletting, and the tabletting pressure varies according to the size of tablets, however, it is generally 200 to 2000 kg/cm$^2$, preferably 250 to 1600 kg/cm$^2$ and more preferably 250 to 1200 kg/cm$^2$.

The rapid disintegrating tablets in oral cavity according to the present invention has a hardness of preferably 1 to 20 kg, more preferably 1 to 15 kg and, still more preferably, 1 to 10 kg. When tablets each having a weight of 200 mg are prepared by compression using, for example, a punch with 8 mm diameter, the hardness is 2 to 15 kg in case the tabletting pressure is 100 to 1,200 kgf and is 3 to 7 kg in case the tabletting pressure is 200 to 800 kgf.

EXAMPLES

The present invention will now be illustrated by way of the following Examples although they are not intended to limit the scope of the present invention.

Evaluation of each tablet prepared in the Examples was carried out according to the following methods.

Oral Disintegration Time

The time from when tablets (one tablet at each test, n=6) were placed in the mouth of 3 to 8 panelists until they were completely disintegrated was measured and its mean value was adopted as an oral disintegration time.

Endothermic Peak of Mannitol

The measurement was carried out by using a differential scanning calorimeter (DSC; TAS-200; manufacture by Rigaku Denki). When mannitol (Mannit P; manufactured by Towa Kasei Kogyo) used as the material was measured by a differential scanning calorimeter, an endothermic peak thereof was 168.8° C.

Hardness of Tablets

Measurement was conducted using a Monsanto hardness meter (manufactured by Kayagaki Irika Kogyo).

Troubles Upon Tabletting

It was observed whether there is adhered matters to upper and lower punches of a tabletting machine (sticking, capping) to evaluate the tabletting troubles.

Example 1

Sorbitol (28 g) was completely dissolved in 600 g of water, then 252 g of mannitol was added thereto and the mixture was homogeneously dispersed by stirring at room temperature at 200 to 300 rpm. The stirring was continued for more 60 minutes to give a dispersion in which sorbitol was dissolved while a part of mannitol was dissolved and remaining part thereof was dispersed. After that, 32 g of crospovidone, 60 g of crystalline cellulose and 28 g of magnesium aluminometasilicate were added thereto and after uniformly dispersed, it is granulated in a spray-drying device to give a composition. Ratio by weight of mannitol/sorbitol in the composition was 90/10. Endothermic peak of the saccharides in the resulting composition was measured by a DSC. The resulting granules (300 parts by weight) were mixed with 1.5 parts by weight of magnesium stearate and subjected to tabletting using a rotary tabletting machine to give tablets each having a weight of 200 mg and a diameter of 8 mm. Oral disintegration time was measured (n=6) for the resulting tablets. The result is shown in Table 1.

Examples 2 and 3

Compositions and tablets were manufactured by the same manner as in Example 1 using the formulations mentioned in Table 1. Oral disintegration time was measured (n=6) for the resulting tablets. The result is shown in Table 1. Ratios by weight of mannitol/sorbitol in the compositions were 95/5 and 85/15.

TABLE 1

|  |  | Examples | | |
|---|---|---|---|---|
|  |  | 1 | 2 | 3 |
| Weight ratio of mannitol/sorbitol | | 90/10 | 95/5 | 85/15 |
| Formulation | Mannitol | 252 | 266 | 238 |
|  | Sorbitol | 28 | 14 | 42 |
|  | Crystalline cellulose | 60 | 60 | 60 |
|  | Crospovidone | 32 | 32 | 32 |
|  | Mg aluminometasillicate | 28 | 28 | 28 |
|  | Total | 400 | 400 | 400 |
| Endothermic peak of saccharides in the composition (° C) | | 164 | 165 | 161 |
| Depression of endothermic peak (° C.) | | 4 | 3 | 7 |
| Oral disintegration time (sec) | | 17 | 18 | 15 |
| Tabletting pressure (kgf) | | 300 | 340 | 275 |
| Tabletting troubles | | None | None | None |

Examples 4 to 8

Compositions and tablets were manufactured by the same manner as in Example 1 using the formulations mentioned in Table 2 except that erythritol was used instead of sorbitol. Oral disintegration time was measured (n=6) for the resulting tablets. The result is shown in Table 2.

TABLE 2

|  |  | Examples | | | | |
|---|---|---|---|---|---|---|
|  |  | 4 | 5 | 6 | 7 | 8 |
| Weight ratio of mannitol/erythritol | | 93/7 | 91/9 | 90/10 | 89/11 | 86/14 |
| Formulation | Mannitol | 260 | 255 | 252 | 250 | 240 |
|  | Erythritol | 20 | 25 | 28 | 30 | 40 |
|  | Crystalline cellulose | 60 | 60 | 60 | 60 | 60 |
|  | Crospovidone | 32 | 32 | 32 | 32 | 32 |
|  | Mg aluminometasillicate | 28 | 28 | 28 | 28 | 28 |
|  | Total | 400 | 400 | 400 | 400 | 400 |
| Endothermic peak of saccharides in the composition (° C.) | | 161 | 161 | 160 | 160 | 159 |
| Depression of endothermic peak (° C.) | | 7 | 7 | 8 | 8 | 9 |
| Oral disintegration time (sec) | | 20 | 16 | 16 | 19 | 17 |
| Tabletting pressure (kgf) | | 275 | 260 | 260 | 265 | 245 |
| Tabletting troubles | | None | None | None | None | None |

From the results of Table 1 and Table 2, it is noted that the compositions where the endothermic peak depression of the saccharides in the composition was within a range of not more than 10° C. show an excellent disintegration in oral cavity. Ratios by weight of mannitol/sorbitol in these cases are 95 to 85/5 to 15.

Examples 9 to 14

Compositions and tablets were manufactured by the same manner as in Example 1 using the formulations mentioned in Table 3 except that the saccharides were changed to lactose, trehalose, maltose, glucose, sucrose and maltitol. Oral disintegration time was measured (n=6) for the resulting tablets. The result is shown in Table 3. Ratio by weight of mannitol/saccharide in the composition is 90/10.

TABLE 3

| | Examples | | | | | |
|---|---|---|---|---|---|---|
| | 9 | 10 | 11 | 12 | 13 | 14 |
| Weight ratio of mannitol/specific saccharide | 90/10 | 90/10 | 90/10 | 90/10 | 90/10 | 90/10 |
| Formulation Mannitol | 252 | 252 | 252 | 252 | 252 | 252 |
| Lactose | 28 | | | | | |
| Trehalose | | 28 | | | | |
| Maltose | | | 28 | | | |
| Glucose | | | | 28 | | |
| Sucrose | | | | | 28 | |
| Maltitol | | | | | | 28 |
| Crystalline cellulose | 60 | 60 | 60 | 60 | 60 | 60 |
| Crospovidone | 32 | 32 | 32 | 32 | 32 | 32 |
| Mg aluminometasillicate | 28 | 28 | 28 | 28 | 28 | 28 |
| Total | 400 | 400 | 400 | 400 | 400 | 400 |
| Endothermic peak of saccharides in the composition (° C.) | 163 | 166 | 165 | 164 | 165 | 166 |
| Depression of endothermic peak (° C.) | 5 | 2 | 3 | 4 | 3 | 2 |
| Oral disintegration time (sec) | 15 | 17 | 17 | 15 | 18 | 16 |
| Tabletting pressure (kgf) | 310 | 315 | 320 | 360 | 370 | 320 |
| Tabletting troubles | None | None | None | None | None | None |

Examples 15 to 18

Compositions and tablets were manufactured by the same manner as in Example 1 using the formulations mentioned in Table 4 except that mannitol and lactose were used as the saccharides and synthetic hydrotalcite, anhydrous calcium hydrogen phosphate, calcium carbonate or talc was used instead of magnesium aluminometasilicate. Oral disintegration time was measured (n=6) for the resulting tablets. The result is shown in Table 4. Ratio by weight of mannitol/saccharide in the composition is 90/10.

TABLE 4

| | Examples | | | |
|---|---|---|---|---|
| | 15 | 16 | 17 | 18 |
| Weight ratio of mannitol/lactose | 90/10 | 90/10 | 90/10 | 90/10 |
| Formulation Mannitol | 252 | 252 | 252 | 252 |
| Lactose | 28 | 28 | 28 | 28 |
| Crystalline cellulose | 60 | 72 | 68 | 68 |
| Crospovidone | 32 | 32 | 32 | 32 |
| Synthetic hydrotalcite | 28 | | | |
| Calcium hydrogen phophate, anhydrous | | 16 | | |
| Precipitated calcium carbonate | | | 20 | |
| Talc | | | | 20 |
| Total | 400 | 400 | 400 | 400 |
| Endothermic peak of saccharides in the composition (° C.) | 164 | 164 | 164 | 164 |
| Depression of endothermic peak (° C.) | 4 | 4 | 4 | 4 |
| Oral disintegration time (sec) | 17 | 14 | 14 | 18 |
| Tabletting pressure (kgf) | 300 | 340 | 350 | 345 |
| Tabletting troubles | None | None | None | None |

Examples 19 to 21

Compositions and tablets were manufactured by the same manner as in Example 1 using the formulations mentioned in Table 5 except that mannitol and lactose were used as the saccharides, magnesium aluminometasilicate was used as an inorganic excipient and crystalline cellulose, low-substituted hydroxypropyl cellulose (L-HPC), crospovidone or croscarmellose was used as a disintegrating agent. Oral disintegration time was measured (n=6) for the resulting tablets. The result is shown in Table 5. Ratio by weight of mannitol/saccharide in the composition is 90/10.

TABLE 5

| | Examples | | |
|---|---|---|---|
| | 19 | 20 | 21 |
| Weight ratio of mannitol/lactose | 90/10 | 90/10 | 90/10 |
| Formulation Mannitol | 252 | 252 | 252 |
| Lactose | 28 | 28 | 28 |
| Mg aluminometasillicate | 28 | 28 | 28 |
| Crystalline cellulose | 60 | 60 | 60 |
| L-HPC | 32 | 16 | |
| Crospovidone | | 16 | |
| Croscarmellose sodium | | | 32 |
| Total | 400 | 400 | 400 |
| Endothermic peak of saccharides in the composition (° C.) | 165 | 165 | 165 |
| Depression of endothermic peak (° C.) | 3 | 3 | 3 |
| Oral disintegration time (sec) | 19 | 14 | 19 |
| Tabletting pressure (kgf) | 300 | 300 | 310 |
| Tabletting troubles | None | None | None |

Example 22

After 40 g of sorbitol was completely dissolved in 600 g of water, 240 g of mannitol was added to disperse therein homogeneously and the mixture was stirred for a while. After that, 32 g of crospovidone, 60 g of crystalline cellulose and 28 g of magnesium aluminometasilicate were added and homogeneously dispersed using a wet-type dispersing device (My Colloider KM; manufactured by Tokushu Kikakogyo). The resulting dispersion was granulated using a spray-drying device (L-8; manufactured by Okawahara Kakoki) to give a composition 1. According to the composition as shown in Table 6, the resulting composition 1, ascorbic acid as a pharmacologically active ingredient and magnesium stearate as a component being able to be used for a medicament were mixed and tabletted using a rotary tabletting machine (with a punch of 8 mm diameter having flat corner) to give tablets each having a weight of 200 mg and a hardness of 3.5 kg. Oral disintegration time of the resulting tablets and the occurrence of obstacles during tabletting are shown in Table 6.

TABLE 6

| Formulation | Granule 1 | 268.5 | 223.5 | 163.5 |
|---|---|---|---|---|
| | L-ascorbic acid | 30 | 75 | 135 |
| | Magnesium stearate | 1.5 | 1.5 | 1.5 |
| Tabletting pressure (kgf) | | 305 | 420 | 680 |
| Hardness of tablets (kg) | | 3.4 | 3.5 | 3.5 |
| Tabletting troubles | | None | None | None |
| Oral disintegration time (sec) | | 15 | 16 | 20 |

Example 23

Tablets were manufactured by the same manner as in Example 22 except that acetaminophen was used instead of L-ascorbic acid. Oral disintegration time of the resulting tablets and the occurrence of obstacles during tabletting are shown in Table 7.

TABLE 7

| Formulation | Granule 1 | 268.5 | 238.5 | 178.5 |
|---|---|---|---|---|
| | Acetaminophen | 40 | 60 | 120 |
| | Magnesium stearate | 1.5 | 1.5 | 1.5 |
| Tabletting pressure (kgf) | | 300 | 405 | 650 |
| Hardness of tablets (kg) | | 3.6 | 3.6 | 3.5 |
| Tabletting troubles | | None | None | None |
| Oral disintegration time (sec) | | 15 | 14 | 20 |

INDUSTRIAL APPLICABILITY

The tablets obtained from the composition for rapid disintegrating tablets in oral cavity according to the present invention is characterized in that it can significantly reduce the oral disintegration time although they have higher hardness compared to the rapid disintegrating tablets of the prior art. Therefore, the tablets of the present invention obtained by adding the pharmacologically active ingredient to the present composition is suitable for medicaments for which an excellent disintegrating property in oral cavity is required. Tablets obtained by using the composition for rapid disintegrating tablets in oral cavity of the invention can be produced, after mixing the present composition, the pharmacologically active ingredient and the component which does not deteriorate a disintegrating property, by a simple method with dry compression molding.

The composition for rapid disintegrating tablets in oral cavity of the present invention makes it possible to obtain tablets exhibiting an especially excellent disintegrating property in oral cavity and can be suitably used for tablets for which rapid disintegrating property in oral cavity is required.

The invention claimed is:

1. A tablet composition which comprises:
   (a) saccharides comprised of a combination of mannitol and one or more of other saccharide(s) selected from sorbitol, erythritol, maltitol, lactose, and trehalose in an amount of 40 to 90 parts by weight;
   (b) an inorganic excipient in an amount of 1 to 30 part(s) by weight; and
   (c) a disintegrating agent in an amount of 5 to 40 parts by weight,
   wherein a total amount of components (a), (b) and (c) is 100 parts by weight,
   wherein a weight ratio of mannitol to other saccharide(s) is (98 to 75): (2 to 25),
   wherein the tablet composition exhibits an oral disintegration time of within 40 seconds, and
   wherein mannitol and other saccharide(s) form complex particles, which exhibit a melting point depression, and the inorganic excipient and the disintegrating agent are dispersed in the complex particles.

2. The composition according to claim 1, wherein:
   (a) saccharides are 50 to 80 parts by weight;
   (b) the inorganic excipient is 2 to 15 parts by weight; and
   (c) the disintegrating agent is 10 to 35 parts by weight.

3. The composition according to claim 1, wherein:
   (a) saccharides are 65 to 80 parts by weight;
   (b) the inorganic excipient is 3 to 10 parts by weight; and
   (c) the disintegrating agent is 17 to 34 parts by weight.

4. The composition according to claim 1, wherein the complex particles form a solid dispersion.

5. The composition according to claim 1, wherein an endothermic peak of the saccharides is shifted to a low temperature side by 0.5 to 10° C. compared to an endothermic peak measured from mannitol only.

6. The composition according to claim 1, wherein the ratio by weight of mannitol to other saccharide(s) is (97 to 75): (3 to 25).

7. The composition according to claim 1, wherein the ratio by weight of mannitol to other saccharide(s) is (96 to 81): (4 to 19).

8. The composition according to claim 1, wherein the inorganic excipient has an average pore diameter of 100 nm or less and is a pharmaceutically acceptable inorganic compound containing any of aluminum, magnesium and calcium.

9. The composition according to claim 1, wherein the inorganic excipient is selected from magnesium aluminometasilicate, magnesium aluminosilicate, synthetic hydrotalcite, calcium silicate, calcium hydrogen phosphate, calcium carbonate, talc and dry aluminum oxide gel.

10. The composition according to claim 1, wherein the disintegrating agent has an average particle diameter of 60 μm or less, and is selected from crospovidone, low-substituted hydroxypropyl cellulose, crystalline cellulose and croscarmellose sodium.

11. The composition according to claim 10, wherein the disintegrating agent has an average particle diameter of 20 μm or less.

12. The composition according to claim 1; wherein the disintegrating agent is crospovidone having an average particle diameter of 20 μm or less and crystalline cellulose having an average particle diameter of 40 μm or less.

13. The composition according to claim 1, which contains 5 to 13 parts by weight of crospovidone and 12 to 21 parts by weight of crystalline cellulose as the disintegrating agent.

14. The composition according to claim 1, which is obtained by spray-drying an aqueous solution or an aqueous dispersion comprising the saccharides, the disintegrating agent and the inorganic excipient.

15. The composition according to claim 14, which is obtained by spray-drying the dispersion obtained by dissolving or dispersing, in advance, mannitol and other saccharide(s) in an aqueous medium and then homogeneously dispersing the disintegrating agent and the inorganic excipient.

16. The composition according to claim 1, which further contains 0.01 to 100 parts by weight of a pharmacologically active ingredient and/or 0.01 to 1000 parts by weight of a component which does not deteriorate a disintegrating property based on 100 parts by weight of a total amount of the saccharides, the inorganic excipient and the disintegrating agent.

17. The tablet composition according to claim 1, wherein the tablet composition exhibits an oral disintegration time of within 30 seconds.

18. The tablet composition according to claim 1, wherein the tablet composition exhibits an oral disintegration time of within 20 seconds.

\* \* \* \* \*